(12) United States Patent
Carlson et al.

(10) Patent No.: US 9,671,323 B2
(45) Date of Patent: Jun. 6, 2017

(54) DETECTION OF FOREIGN MATERIAL ON A SUBSTRATE CHUCK

(71) Applicant: GLOBALFOUNDRIES INC., Grand Cayman (KY)

(72) Inventors: Robert G. Carlson, Fairfax, VT (US); Bradley M. Mahan, Burlington, VT (US)

(73) Assignee: GLOBALFOUNDRIES Inc., Grand Cayman (KY)

( * ) Notice: Subject to any disclaimer, the term of this patent is extended or adjusted under 35 U.S.C. 154(b) by 220 days.

(21) Appl. No.: 14/705,065

(22) Filed: May 6, 2015

(65) Prior Publication Data

US 2016/0327462 A1    Nov. 10, 2016

(51) Int. Cl.
| G01N 3/04 | (2006.01) |
| G01N 19/08 | (2006.01) |
| H01L 21/67 | (2006.01) |

(52) U.S. Cl.
CPC .............. *G01N 3/04* (2013.01); *G01N 19/08* (2013.01); *H01L 21/67288* (2013.01)

(58) Field of Classification Search
CPC ...................................................... G01N 3/04
See application file for complete search history.

(56) References Cited

U.S. PATENT DOCUMENTS

| 5,859,924 A | 1/1999 | Liu et al. |
| 6,850,377 B2 | 2/2005 | Hashi et al. |
| 2009/0103079 A1* | 4/2009 | Uto .................... G01N 21/9501 356/237.4 |
| 2014/0370794 A1 | 12/2014 | Fukushima et al. |

FOREIGN PATENT DOCUMENTS

| JP | 07130638 | 5/1995 |
| JP | 09181086 | 7/1997 |
| JP | 11214468 | 8/1999 |
| JP | 2014175614 | 9/2014 |
| KR | 2019990037252 | 10/1999 |

OTHER PUBLICATIONS

Anonymous; A Technique for Isolating Contamination on Wafer Chucks; IP.com; IP.com No. 000041169; Feb. 2, 2005; 2 pages.
Anonymous; Automatic Detection and Control of Foreign Objects or Insufficient Clearance in Test Fixtures; IP.com; IP.com No. 000181993; Apr. 21, 2009; 8 pages.

* cited by examiner

*Primary Examiner* — Clayton E Laballe
*Assistant Examiner* — Dennis Hancock
(74) *Attorney, Agent, or Firm* — Thompson Hine LLP; Anthony Canale

(57) ABSTRACT

A method and apparatus for determining the presence of foreign material on a substrate chuck. The method includes: placing a bottom surface of a substrate on a top surface of the substrate chuck; applying a lateral force in a direction parallel to a top surface of the substrate chuck to the substrate; when the substrate moves partially off or moves completely off the substrate chuck in response to the applying the lateral force then a defect is present between the top surface of the substrate chuck and the bottom surface of the substrate; or when the substrate remains completely on the substrate chuck in response to the applying the lateral force then a defect is not present between the top surface of the substrate chuck and the bottom surface of the substrate.

20 Claims, 7 Drawing Sheets

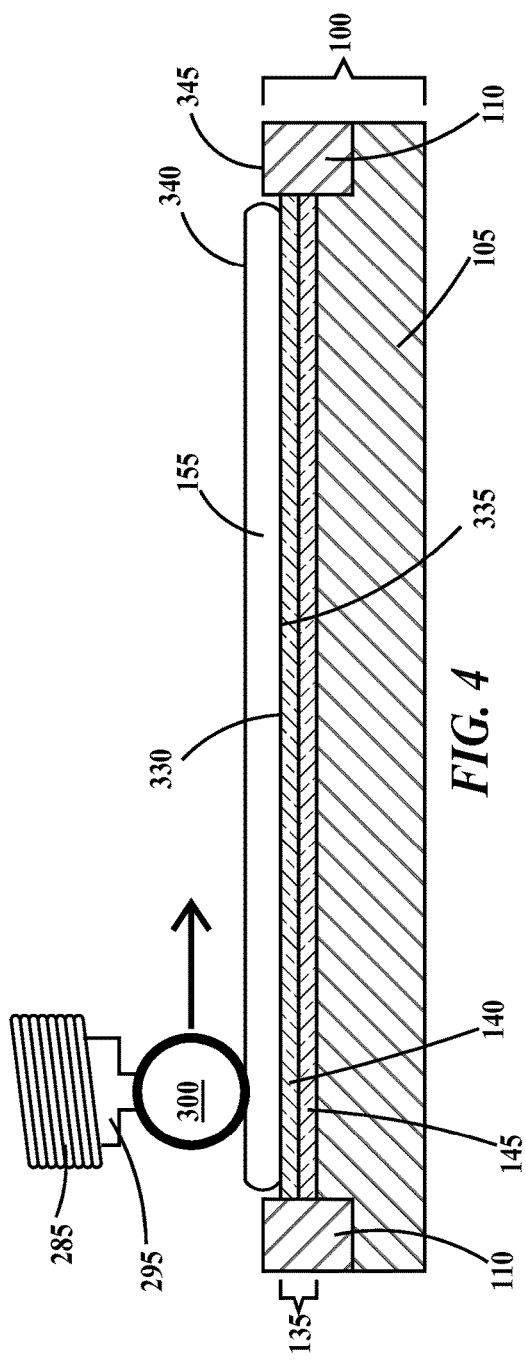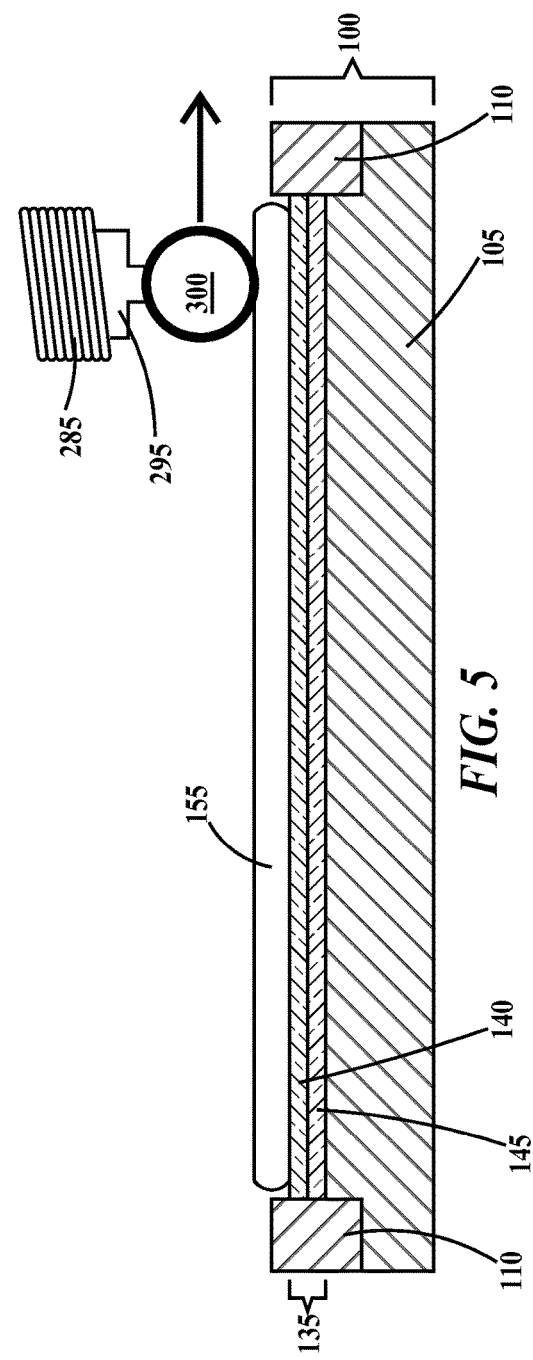

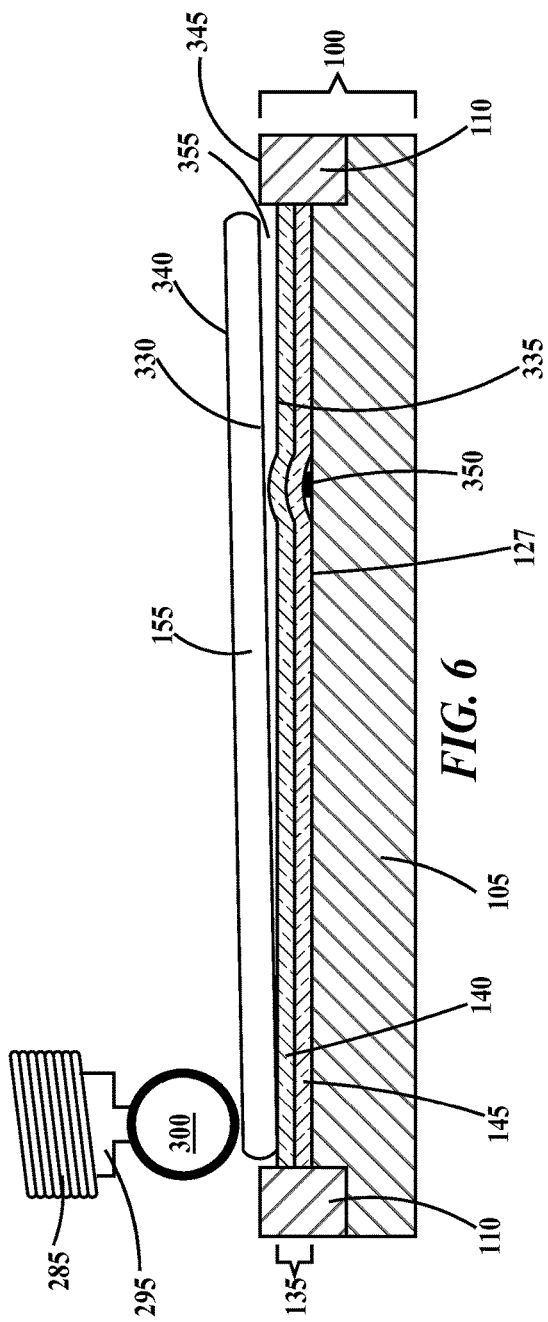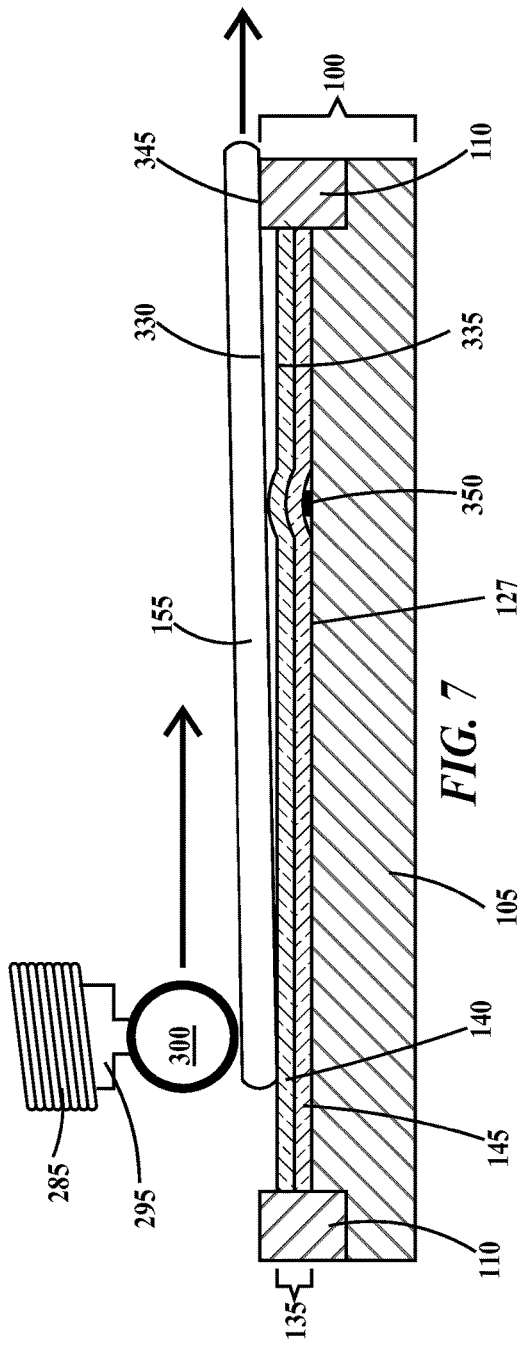

DETECTION OF FOREIGN MATERIAL ON A SUBSTRATE CHUCK

BACKGROUND

The present invention relates to the field of integrated circuit manufacture; more specifically, it relates to an apparatus for detecting foreign material under a resilient film adhesively attached to a substrate chuck and method of using the apparatus.

The adhesive backed film on the surface of substrate chucks must be removed and replaced periodically. During the replacement process foreign material can become lodged between the surface of the chuck and the adhesive layer causing a bump in the film which will cause the substrate to be held improperly by the chuck causing misprocessing or damage to the substrate and/or devices (e.g. integrated circuit chips) being fabricated on the substrate. Currently no repeatable method exists for detecting foreign material lodged between the surface of the chuck and the adhesive layer. Accordingly, there exists a need in the art to eliminate the deficiencies described hereinabove.

BRIEF SUMMARY

A first aspect of the present invention is a method for determining the presence of foreign material on a substrate chuck, comprising: placing a bottom surface of a substrate on a top surface of the substrate chuck; applying a lateral force in a direction parallel to a top surface of the substrate chuck to the substrate; when the substrate moves partially off or moves completely off the substrate chuck in response to the applying the lateral force then a defect is present between the top surface of the substrate chuck and the bottom surface of the substrate; or when the substrate remains completely on the substrate chuck in response to the applying the lateral force then a defect is not present between the top surface of the substrate chuck and the bottom surface of the substrate.

A second aspect of the present invention is an apparatus for determining the presence of foreign material on a substrate chuck, comprising: the substrate chuck configured to hold a substrate; means for applying a lateral force in a direction parallel to a top surface of the substrate chuck to the substrate when the substrate is on the substrate chuck; and means for applying a downward force in a direction perpendicular to a top surface of the substrate chuck to the substrate when the substrate is on the substrate chuck.

These and other aspects of the invention are described below.

BRIEF DESCRIPTION OF THE DRAWINGS

The features of the invention are set forth in the appended claims. The invention itself, however, will be best understood by reference to the following detailed description of illustrative embodiments when read in conjunction with the accompanying drawings, wherein:

FIGS. 4 and 5 are cross-section views illustrating the effect of the apparatus of FIGS. 2 and 3 on the substrate chuck of FIGS. 1A and 1B with no foreign material according to an embodiment of the present invention;

FIGS. 6 and 7 are cross-section views illustrating the effect of the apparatus of FIGS. 2 and 3 on the substrate chuck of FIGS. 1A and 1B with foreign material according to an embodiment of the present invention;

DETAILED DESCRIPTION

Chemical mechanical polishing (CMP) requires that substrates (e.g., circular semiconductor wafers) be held on a chuck while the wafer is positioned frontside down on the CMP polishing pad. Vacuum, air or water may be applied though the chuck to the backside of the substrate during the CMP process. To protect the wafer and avoid direct contact between the wafer and chuck a pad including an adhesive backed film is applied to the top surface of the chuck (so as to lie between the top surface of the chuck and the backside of the wafer). If foreign material (air or liquid bubbles between the chuck and adhesive backed film or in the adhesive backed film are also defined as foreign material) becomes lodged between the top surface of the chuck and the adhesive layer a bump will be formed in the film over the foreign material. The bump will cause the wafer not to lie flat on the film resulting in the wafer not being held firmly and inconsistent polishing across the surface of the wafer when the chuck is used in a CMP tool.

The apparatus according to the embodiments of the present invention detects the presence of a bump in the film by taking advantage of the fact that a test wafer will not lie flat on the chuck but be slightly tilted if foreign material is present under the film or foreign material is present on the surface of the film. A probe tip provides a lateral force to the surface of a test wafer when the probe tip is dragged across the top surface of the test wafer. If foreign material is present the wafer will not sit flat on the film and the wafer will be slid off the chuck as the probe tip is moved. If there is no foreign material present the wafer will sit flat on the film and the wafer will not be slid off the chuck as the probe tip is moved. The probe tip provides frictional contact to the surface of the test wafer and is attached to a spring that presses the probe tip against the wafer surface. The spring and probe tip are dragged along the surface of the test wafer by a rotatable swing arm.

The apparatus will detect anything that causes the test wafer not to sit flat on the chuck including foreign material between the adhesive and film and foreign material in the adhesive film. The apparatus will detect foreign material on chucks that do not use a resilient film. e.g., chucks where the surface of the chuck contacts the substrate directly. However, while foreign material on the film surface can be detected visually it is more difficult to visually detect foreign material or bubbles under or in the adhesive film. The embodiments of the present invention are not limited to semiconductor wafers but may be adapted to substrate of other materials and shapes.

Figure 1A:
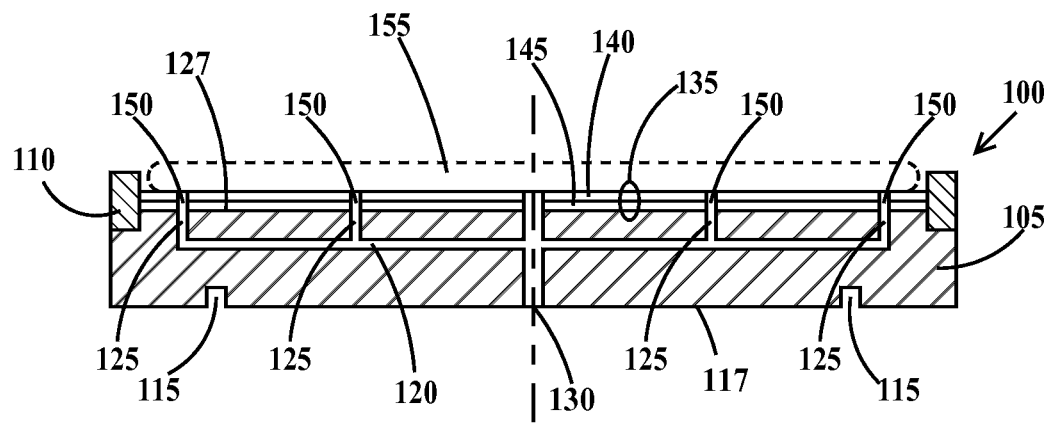
FIG. 1A is a cross section through line 1A-1A of the top view of FIG. 1B of an exemplary substrate chuck.
Figure 1B:
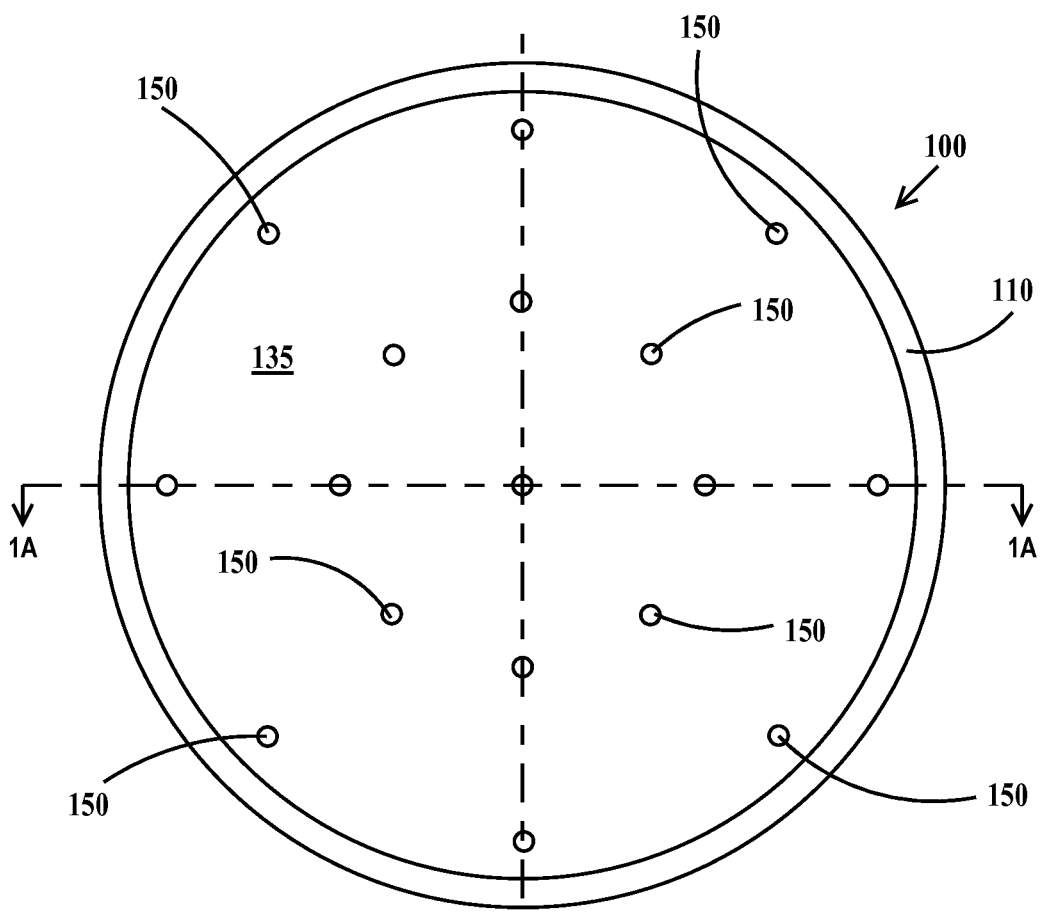

FIG. 1A is a cross section through line 1A-1A of the top view of FIG. 1B of an exemplary substrate chuck. In FIGS. 1A and 1B, a circular substrate chuck 100 includes a chuck body 105 having a fixed ring 110 around the periphery of the chuck and locating notches 115 in a bottom surface 117 of the chuck. Chuck body 105 is provided with channels 120 connected to ports 125 open to a top surface 127 of chuck 100. Channel 120 is also connected to a backside port 130 in bottom surface 117. A pad 135 including a film 140 and an adhesive layer 145 is illustrated attached (by the adhesive layer) to top surface 127 of chuck 100. Holes 150 in pad 135 align with ports 125 in chuck 100. Holes 150 pass completely through film 140 and adhesive layer 145. In one example, film 140 is formed from plastic, elastomer or other polymer. In one example, film 140 is resilient. A wafer 155 (dotted lines) is illustrated in place on pad 135. Wafer 155 is centered on chuck 100.

Figure 2:
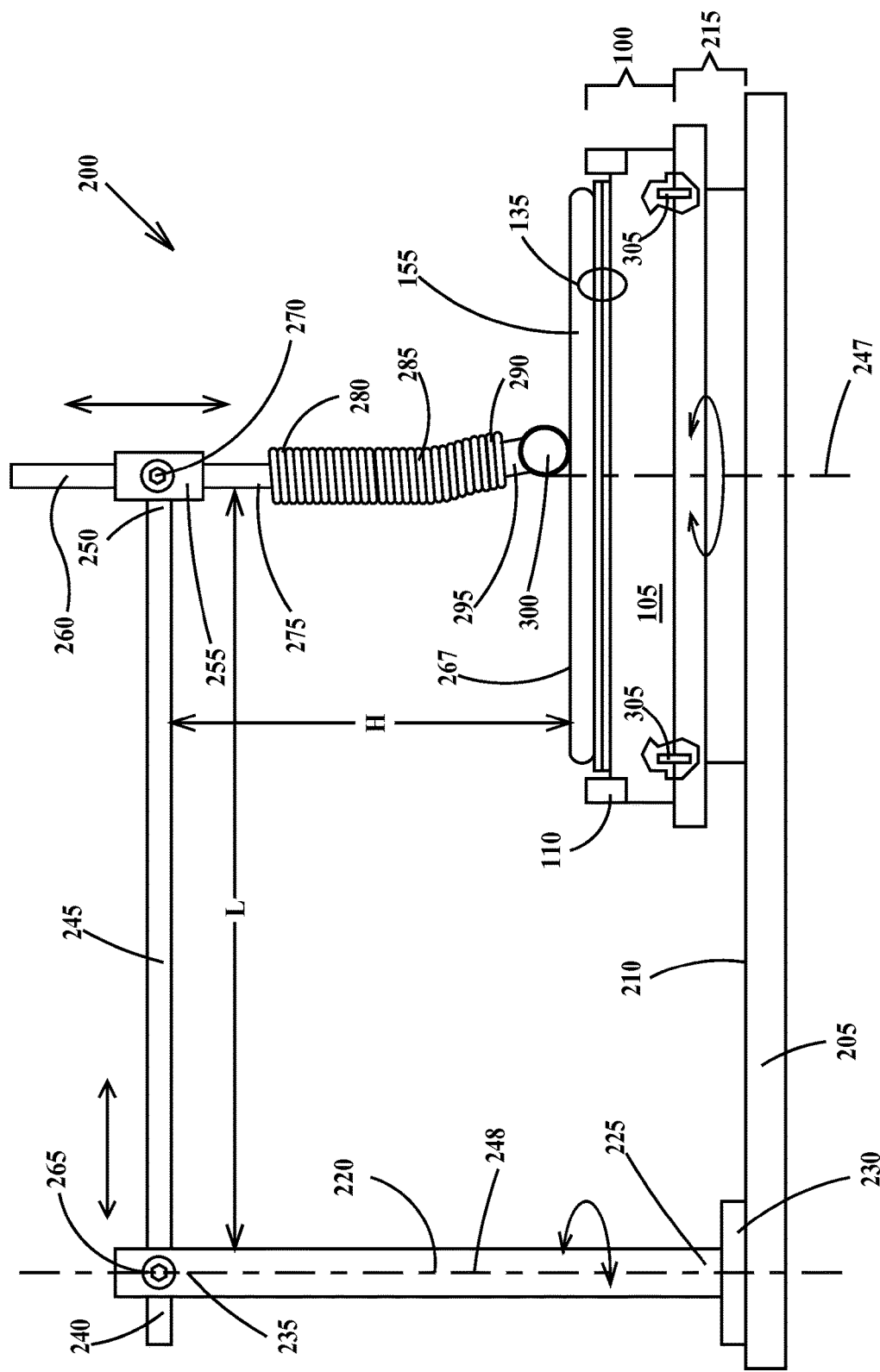
FIG. 2 is a side view of an apparatus for detecting foreign material on the substrate chuck of FIGS. 1A and 1B according to an embodiment of the present invention.

FIG. 2 is a side view of an apparatus for detecting foreign material on the substrate chuck of FIGs. 1A and 1B according to an embodiment of the present invention. In FIG. 2, an apparatus 200 is holding wafer chuck 100 which in turn is holding wafer 155. Apparatus 200 includes a base 205 having a top 210 surface 210, a turntable 215 attached to base 205, a vertical post 220 having a lower end 225 mounted to base 205 by a flange 230 and an upper end 235 bored to accept a first end 240 of a horizontal swing arm 245. Top surface 210 defines a horizontal reference plane with horizontal directions being parallel to the reference plane and vertical directions and rotational axes being perpendicular to the reference plane. Turntable 215 is rotatable 360° about a vertical axis 247 passing through the center of turntable 215 and chuck 100. Post 220 is rotatable at least 90° about a vertical axis 248. A second end 250 of arm is fixed to a slide 255. Slide 255 is bored to accept a vertical rod 260. The distance L between post 220 and rod 260 is adjustable by sliding swing arm in or out of the bore in upper end 235 of post 220 and is held in position by screw 265. The height H of swing arm 245 above top surface 267 of wafer 155 is adjustable by sliding rod 260 up and down in slide 255 and is held in position by screw 270 to prevent up and down and rotational movement of rod 260. A lower end 275 of rod 260 is attached by to an upper end 280 of a spring 285. A lower end 290 of spring 285 is attached by connector 295 to a probe tip 300. The height H is adjusted to spring 285 flexes to push probe tip 300 against top surface 167 of wafer 155. The amount of force applied by spring 285 is set by adjusting the height H and the spring constant of spring 285. Probe tip 300 provides a frictional interface to wafer 155. Probe tip 300 applies a lateral (horizontal) force to wafer 155 when swing arm 245 is swept through a circular arc by rotating post 220. In one example, probe tip 300 is a sphere. In one example, probe tip 300 is formed from plastic, elastomer or other polymer. In one example, probe tip is resilient. In one example, probe tip is formed from silicone. In one example, chuck 100 is temporally held in position on turntable 215 by locating pins 305. The combination of swing arm 245, rod 260, spring 285 and probe tip 300 apply both lateral and downward forces to wafer 155.

Figure 3:
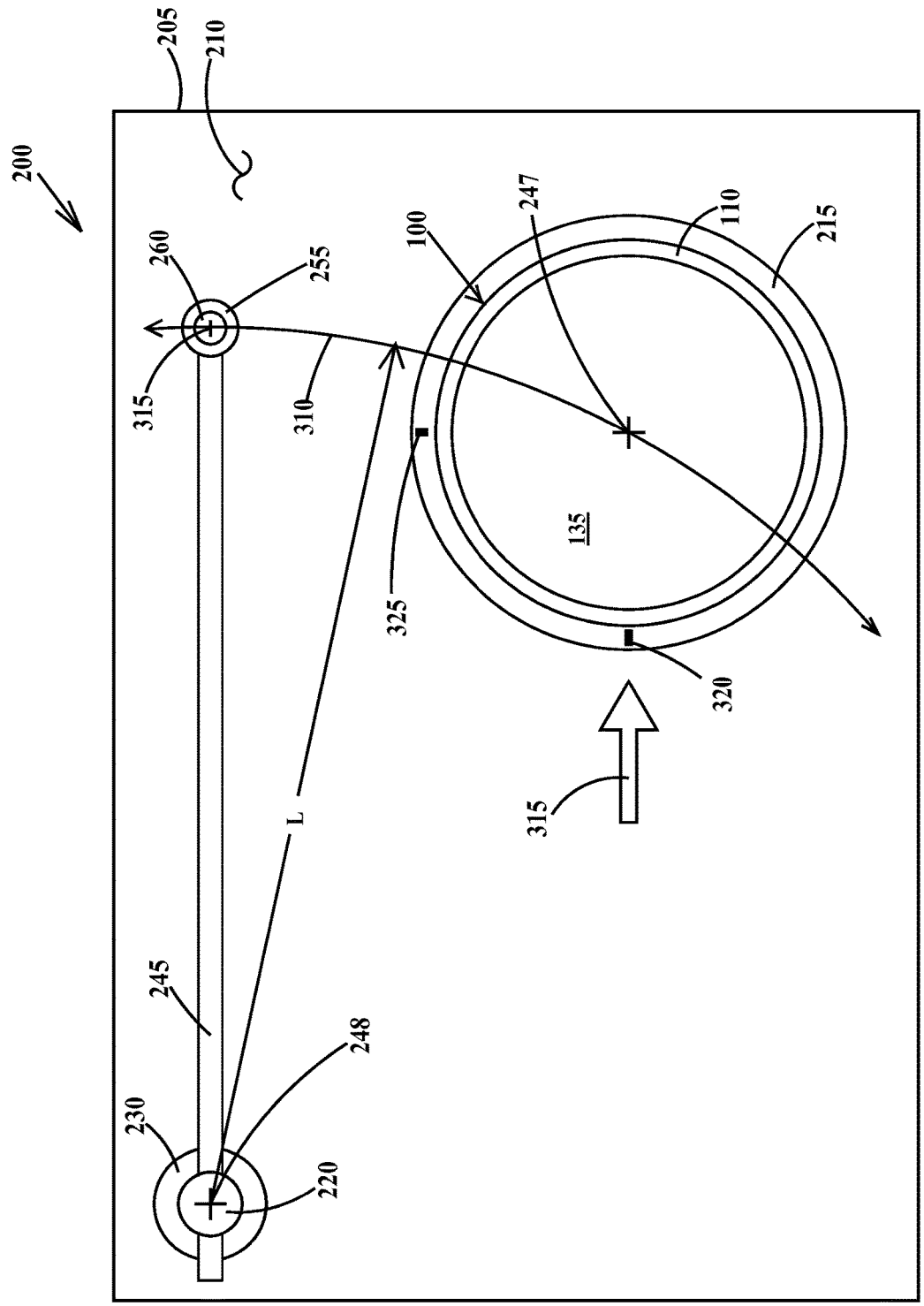
FIG. 3 is a top view of an apparatus of FIG. 2 according to an embodiment of the present invention.

FIG. 3 is a top view of an apparatus of FIG. 2 according to an embodiment of the present invention. In FIG. 3, it can be seen that swing arm 245 can rotate about axis 248 so as to swing rod 260 in and arc 310 of length L over chuck 100. Swing arm 245 is illustrated in a home position. In the example of FIG. 3, length L has been adjusted so a center of 315 of rod 260 passes directly over or proximate to axis 247. Alternatively, the length L can be adjusted so probe tip 300 (see FIG. 2) passes directly over or proximate to axis 247. The top 210 of table 205 has indicia 315. Turntable 100 includes two marks 320 and 325 located 90° apart. In use, a wafer is placed on pad 135 and the turntable rotated by a human operator so mark 320 aligns to indicia 315. Swing arm 245 is in a home position. While holding turntable 100 so it can not rotate, the operator moves swing arm 245 through an arc so probe tip 300 (see FIG. 2) is dragged onto the wafer surface, dragged across the wafer surface and off the wafer past the edge of the wafer. If the wafer is still in position then the swing arm is moved back across the surface in the opposite direction to its home position. If the wafer is still in place on turntable 100 the operator rotates chuck 100 so indicia 315 is aligned with mark 325 and again holding turntable 100 so it can not rotate moves swing arm 245 through an arc so probe tip 300 (see FIG. 2) is dragged onto the wafer surface, dragged across the wafer and dragged off the wafer past the edge of the wafer back to a home position. If the wafer is still in position then the swing arm is again moved back across the surface in the opposite direction to its home position. In total, the probe tip crosses the wafer surface four times, twice each for each of mark to indicia alignment.

FIGS. 4 and 5 are cross-section views illustrating the effect of the apparatus of FIGS. 2 and 3 on the substrate chuck of FIGS. 1A and 1B with no foreign material according to an embodiment of the present invention. In FIG. 4, the entire bottom surface 330 of wafer 330 sits flat on the top surface 335 of film 140. As probe tip 300 is started to be dragged across the top surface 340 of wafer 155. In FIG. 5, probe tip 300 has been dragged to the opposite side of wafer 155 and wafer 155 remains in place on chuck 100 because a top surface 345 of rim 110 extends above top surface 335 of film 140 more than bottom surface 330 of wafer 155. The height of ring 110 above the bottom surface 330 of wafer 155 prevents lateral (horizontal) displace of wafer 155 off the chuck.

FIGS. 6 and 7 are cross-section views illustrating the effect of the apparatus of FIGS. 2 and 3 on the substrate chuck of FIGS. 1A and 1B with foreign material according to an embodiment of the present invention. In FIG. 6, the entire bottom surface 330 of wafer 330 does not sit flat on the top surface 335 of film 140 because of foreign material 350 between the top surface 127 of body 105 of chuck 100 and adhesive layer 145. As probe tip 300 is started to be dragged across the top surface 340 of wafer 155 a gap 355 is created (if it does not already exist just due to the presence of foreign material 350) on the side of the wafer opposite from probe tip 300. In FIG. 7, probe tip 300 has been dragged further onto wafer 155 and wafer 155 has been dragged by probe tip 300 so the opposite side of wafer 155 from probe tip 300 is coming off chuck 100. Ring 110 is not sufficiently high above the bottom surface 330 of wafer 155 relative to top surface 127 to prevent lateral (horizontal) displacement of wafer 155 off chuck 100. Depending upon the size and location of foreign material 350, probe tip 300 may have to be dragged further onto wafer 155 then illustrated in FIG. 7 before wafer 155 starts to slide off chuck 100. Wafer 155 may be slid entirely or only partially off chuck 100 after a complete swing of swing arm 245 (see FIG. 2 and description supra is completed). Any movement of wafer 155 off chuck 105 or even onto ring 110 is indicative of a failure of the chuck 100/pad 135 assembly.

Figure 8A:
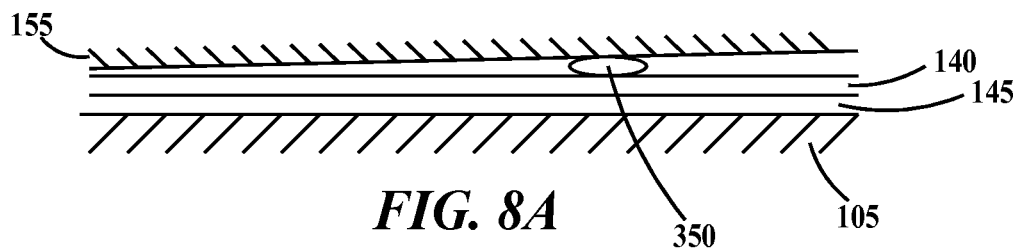
FIGS. 8A, 8B, 8C and 8D illustrate alternative locations of foreign material.
Figure 8B:
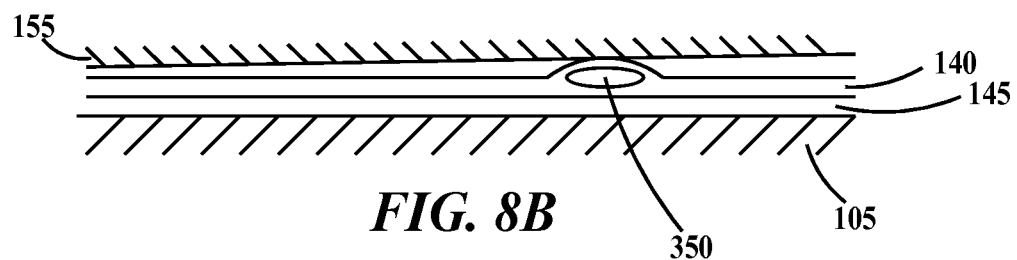
Figure 8C:
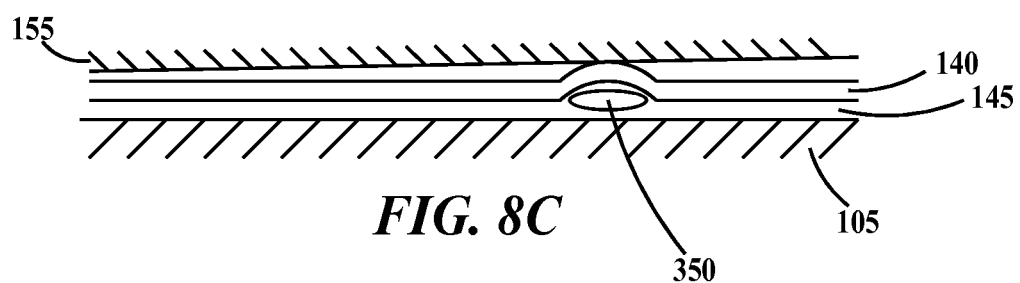
Figure 8D:
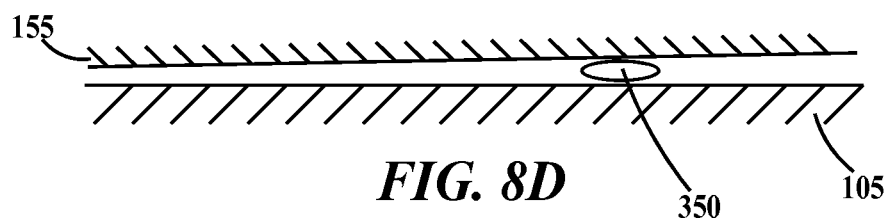

FIGS. 8A, 8B, 8C and 8D illustrate alternative locations of foreign material. In FIG. 8A, foreign material 350 is located on the top surface of film 350 causing wafer 155 to tilt relative to the top surface of body 350. In FIG. 8B, foreign material 350 is located in film 350 causing wafer 155 to tilt relative to the top surface of body 350. In FIG. 8C, foreign material 350 is located in adhesive layer 145 causing wafer 155 to tilt relative to the top surface of body 350. In FIG. 8D, foreign material 350 is located on the top surface of body 350 (there is no adhesive film present) causing wafer 155 to tilt relative to the top surface of body 350.

Figure 9:
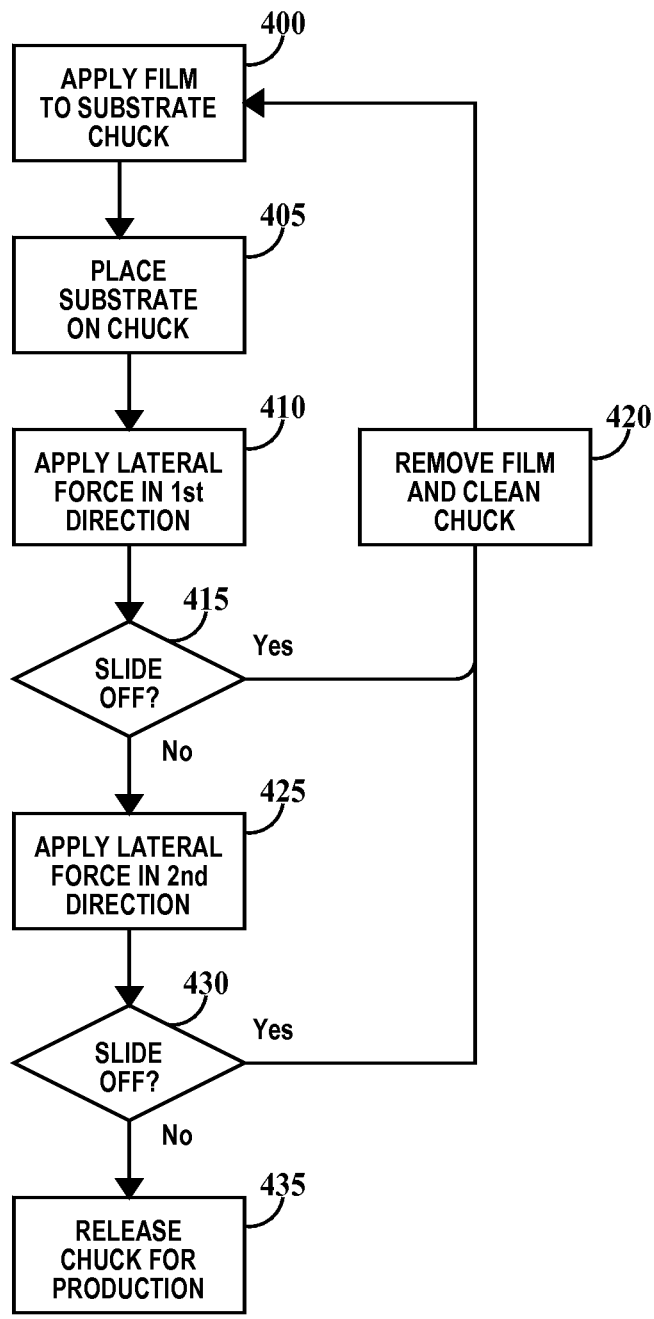
FIG. 9 is a flowchart of the method of using the apparatus of FIGS. 2 and 3 according to an embodiment of the present invention.

FIG. 9 is a flowchart of the method of using the apparatus of FIGS. 2 and 3 according to an embodiment of the present invention. In step 400, a film is attached to the surface of a cleaned chuck by an adhesive layer. In step 405, a test substrate (e.g. semiconductor wafer) is placed on the film on the chuck. In step 410, a lateral force is applied across the surface of the wafer from a home position in a first direction. Optionally a lateral force may be then applied in a direction opposite to the first direction. If in step 415 the wafer slides completely or partially off the chuck the method proceeds to step 420. In step 420, the film and adhesive is removed from the chuck and the chuck cleaned and the method loops back to step 400. Returning to step 415, if in step 415 the wafer remains completely on the chuck the method proceeds to step 425. In step 425, a lateral force is applied across the surface of the wafer in a second direction different from the first direction. In one example, the angle between the first and second direction is between 45 degrees and 135 degrees. Optionally a lateral force may be then applied in a direction opposite to the second direction. The change from the first direction to the second direction is accomplished by rotating the turntable the chuck is mounted on. If in step 430 the wafer slides completely or partially off the chuck the method proceeds to step 420. If in step 430 the wafer remains completely on the chuck the method proceeds to step 435. In step 435 the chuck is released for production. While two tests (steps 410/415 and 425/430) are illustrated in FIG. 8, there may be only one test or there may be more than two tests and the direction of the test for multiple tests may be the same or different. The same test may also be repeated.

Therefore, the embodiments of the present invention provide an apparatus and method for detecting foreign material on a chuck and particularly for detecting foreign material lodged between the surface of the substrate chuck and an adhesive layer attaching a film to the chuck.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for determining the presence of foreign material on a substrate chuck, comprising:
    placing a bottom surface of a substrate on a top surface of said substrate chuck;
    applying a lateral force in a direction parallel to a top surface of said substrate chuck to said substrate;
    when said substrate moves partially off or moves completely off said substrate chuck in response to said applying said lateral force then a defect is present between said top surface of said substrate chuck and said bottom surface of said substrate; or
    when said substrate remains completely on said substrate chuck in response to said applying said lateral force then a defect is not present between said top surface of said substrate chuck and said bottom surface of said substrate.

2. The method of claim 1, wherein said applying said lateral force comprises moving a resilient probe tip in contact with said top surface of said substrate in a direction parallel to said top surface of said substrate chuck.

3. The method of claim 1, wherein said applying said lateral force comprises using an apparatus comprising a resilient probe tip mounted to a first end of spring, a second end of said spring mounted to a rotatable swing arm and including:
    moving said swing arm over said substrate at a designated height above said substrate that allows said spring to apply a downward force on said top surface of said substrate.

4. The method of claim 3, wherein said probe tip moves in an arc over said substrate as said swing arm is moved over said substrate.

5. The method of claim 3, wherein said probe tip moves in an arc that passes over a center of said substrate chuck as said swing arm is moved over said substrate chuck or wherein said probe tip moves in an arc that passes over a region of said substrate chuck proximate to a center of said substrate chuck as said swing arm is moved over said substrate chuck.

6. The method of claim 1, wherein said substrate chuck comprises a body and a removable adhesive backed film applied to said body, a top surface of said film being said top surface of said substrate chuck.

7. The method of claim 1, wherein said substrate chuck includes a raised ring around a perimeter of said substrate chuck, a first height of a top surface of said ring above said top surface of said substrate chuck designed to be less than a second height of said top surface of said substrate chuck when said substrate is on said substrate chuck and no foreign material is present between said substrate chuck and said substrate.

8. The method of claim 1, further including:
    placing said substrate chuck on a turntable;
    wherein said applying said lateral force is applied in a first direction;
    when said substrate remains completely on said substrate chuck in response to said applying said lateral force then rotating said turntable between 45 degrees and 135 degrees;
    applying a second lateral force in a second direction parallel to said top surface of said substrate chuck;
    when said substrate moves partially off or moves completely off said substrate chuck in response to said applying said second lateral force then a defect is present between said top surface of said substrate chuck and said bottom surface of said substrate; or
    when said substrate remains completely on said substrate chuck in response to said applying said second lateral force then a defect is not present between said top surface of said substrate chuck and said bottom surface of said substrate.

9. The method of claim 1, wherein said substrate is a circular semiconductor wafer.

10. The method of claim 1, wherein said probe tip is a silicone ball in frictional contact with said top surface of said substrate.

11. An apparatus for determining the presence of foreign material on a substrate chuck, comprising:
    said substrate chuck configured to hold a substrate;
    means for applying a lateral force in a direction parallel to a top surface of said substrate chuck to said substrate when said substrate is on said substrate chuck; and means for applying a downward force in a direction perpendicular to a top surface of said substrate chuck to said substrate when said substrate is on said substrate chuck.

12. The apparatus of claim 11, wherein said means for applying said lateral force and said means for applying said downward force include a resilient probe tip mounted to a first end of a spring, and wherein said spring applies a downward force on said top surface of said substrate.

13. The apparatus of claim 12, wherein said means for applying said lateral force includes a rotatable swing arm adjustable to a designated height over said substrate, a second end of said spring coupled to said swing arm.

14. The apparatus of claim 12, wherein said probe tip is moveable in an arc over said substrate chuck.

15. The apparatus of claim 12, wherein said probe tip is moveable in an arc that passes over a center of said substrate chuck or wherein said probe tip is moveable in an arc that passes over a region of said substrate chuck proximate to a center of said substrate chuck.

16. The apparatus of claim 11, wherein said substrate chuck comprises a body and a removable adhesive backed film applied to said body, a top surface of said film being said top surface of said substrate chuck.

17. The apparatus of claim 11, wherein said substrate chuck includes a raised ring around a perimeter of said substrate chuck, a first height of a top surface of said ring above said top surface of said substrate chuck designed to be less than a second height of said top surface of said substrate when said substrate is on said substrate chuck and no foreign material is present between said substrate chuck and said substrate.

18. The apparatus of claim 11, further including a turntable configured to hold said substrate chuck.

19. The apparatus of claim 11, wherein said substrate is a circular semiconductor wafer.

20. The apparatus of claim 11, wherein said means for applying said lateral force and said means for applying a downward force include a silicone ball in frictional contact with said top surface of said substrate when said substrate is on said substrate chuck.

* * * * *